Figure 1:
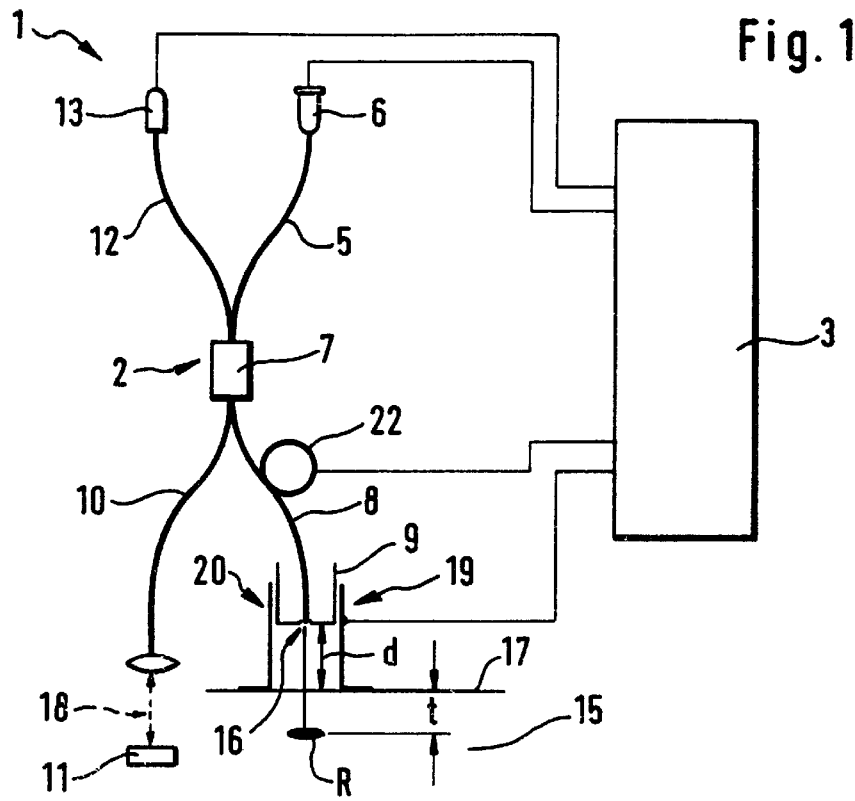

United States Patent

Knuettel et al.

Patent Number: 6,144,449
Date of Patent: Nov. 7, 2000

[54] LOW COHERENCE INTERFEROMETRIC DEVICE

[75] Inventors: Alexander Knuettel, Weinheim; Dirk Boecker, Heidelberg, both of Germany

[73] Assignee: Boehringer Mannheim GmbH, Mannheim, Germany

[21] Appl. No.: 08/875,351

[22] PCT Filed: Jan. 23, 1997

[86] PCT No.: PCT/DE97/00167

§ 371 Date: Jul. 28, 1997

§ 102(e) Date: Jul. 28, 1997

[87] PCT Pub. No.: WO97/27468

PCT Pub. Date: Jul. 31, 1997

[30] Foreign Application Priority Data

Jan. 26, 1996 [DE] Germany .......................... 196 02 785

[51] Int. Cl.[7] .................................................. G01B 9/02
[52] U.S. Cl. ........................ 356/345; 356/357; 356/360
[58] Field of Search .................................. 356/345, 357, 356/360; 385/12, 14

[56] References Cited

U.S. PATENT DOCUMENTS

| 5,073,023 | 12/1991 | Valette et al. | 356/345 |
|---|---|---|---|
| 5,289,256 | 2/1994 | Gramling | 356/345 |
| 5,459,570 | 10/1995 | Swanson et al. | 356/345 |

FOREIGN PATENT DOCUMENTS

| 25 28 209 | 12/1976 | Germany . |
|---|---|---|
| 32 01 801 | 9/1983 | Germany . |
| 42 04 521 | 6/1993 | Germany . |

OTHER PUBLICATIONS

Danielson et al., Applied Optics, vol. 26, No. 14, Jul. 15 1987, Guided–wave reflectometry with micrometer resolution.

Schmitt et al., Applied Optics, vol. 32, No. 30, Oct. 20 1993, "Measurement of optical properties of biological tissues by low–coherence reflectometry".

PCT International Application No. WO 95/30368 published Nov. 16, 1995.

PCT International Application No. WO 92/19930 published Nov. 12, 1992.

(List continued on next page.)

Primary Examiner—Robert H. Kim
Assistant Examiner—Andrew H. Lee
Attorney, Agent, or Firm—Arent Fox Kintner Plotkin & Kahn PLLC

[57] ABSTRACT

Low coherence interferometer apparatus for investigation of a sample (15), in particular for multidimensional imaging, having an interferometer configuration (2) comprising a low coherence light source, a probe head (9) having a light exit opening (16) for irradiating light into the sample, an optical coupler, a reference reflector and a detector (13). The optical paths between the elements of the interferometer configuration (2) form interferometer arms. The optical coupler and the reference arm of the interferometer configuration (2) are integrated into a common optical chip (28). In addition to the reference reflector (11), the reference arm comprises a deflection reflector (33) formed on an end surface (35) of the optical chip (28) in such a manner that the reference light is cross-coupled between a first light guide (10a) forming a first portion of the reference arm (10) and a second light guide (10b) forming a second portion of the reference arm (10).

13 Claims, 5 Drawing Sheets

OTHER PUBLICATIONS

Article by Prof. Dr. Karl Joachim Ebeling.

Jungbluth et al., Laser Focus World, Apr. 1994, "Optical waveguides advance to meet fiberoptic demands".

Proceedings of the Third European Conference, ECIO'85, Berlin, Germany, May 6–8, 1985, Integrated Optics.

Rickman, Sensor Review, vol. 14, No. 1, 1994, pp 27–29, "Silicon Integrated Optics and Sensor Applications".

Brooks et al., Optics Letters, vol. 20, No. 4, Feb. 15, 1995, "Integrated–optic dispersion compensator that uses chirped gratings".

Youngquist et al., Optics Letters, vol. 12, No. 3, Mar. 1987, "Optical coherence–domain reflectometry: a new optical evaluation technique".

Hill et al., Optics Letters, vol. 19, No. 17, Sep. 1, 1994, "Chirped in–fiber Bragg gratings for compensation of optical–fiber dispersion".

Missig et al., Applied Optics, vol. 34, No. 14, May 10, 1995, "Diffractive optics applied eyepiece design".

Shibata et al., J. Opt. Soc. Am. A., vol. 4, No. 3, Mar. 1987, "Temporal coherence properties of a dispersively propagating beam in a fiber–optic interferometer".

Hebden et al., Physic World, Aug. 1993, "Infrared lasers muscle in on medical imaging".

Takada et al., Applied Optics, May 1, 1987, vol. 26, No. 9, "New measurement system for fault location in optical waveguide devices based on an interferometric technique".

Saleh et al., Journal of Lightwave Technology, vol. 6, No. 3 Mar. 1988, "Reflective Single–Mode Fiber–Optic Passive Star Couplers".

Himeno et al., Journal of Lightwave Technology, Jan. 6, 1988, No. 1, vol. 6, "Loss Measurement and Analysis of High–Silica Reflection Bending Optical Waveguides".

LOW COHERENCE INTERFEROMETRIC DEVICE

The invention concerns a low coherence interferometer apparatus for the investigation of a sample, in particular for multi-dimensional imaging in medical applications.

Low coherence interferometer methods are used for a variety of applications. They are normally referred to in the art as LCI (Low Coherence Interferometry) methods or as OCDR (Optical Coherence Domain Reflectometry). The abbreviation LCI is used below for reasons of simplicity.

LCI methods are utilized or are at least discussed for a variety of applications. For example, reference can be made to the following citations:

1) Danielson et al: "Guide-wave Reflectometry with Micrometer Resolution", Applied Optics, 26 (1987), 2836–2842.
2) Schmitt et al: "Measurement of Optical Properties of Biological Tissues by Low-Coherence Reflectometry", Applied Optics, 32 (1993), 6032–6042
3) WO 95/30368
4) DE 2528209 A
5) DE 3201801 A1
6) WO 92/19930
7) DE 4204521C1
8) U.S. Pat. No. 5,073,024

All LCI methods have the common property that light from a low coherence (wide spectral band width emitting) light source is split into two partial beams—a measuring light beam and a reference light beam. The two beams are joined upstream of a detector to produce an interference signal containing the desired information. A principal component in the low coherence interferometry apparatus (designated below as "LCI apparatus") is an interferometer configuration comprising, in addition to the low coherence light source, an optical coupler, a reference reflector, a probe head having a light exit opening for irradiating light into the sample, and the detector.

The optical paths between these interferometer elements form so-called interferometer arms. Light from the light source passes through the light source arm and is incident on the optical coupler where it is split. One part, constituting measuring light, passes through a sample arm and the probe head and is irradiated into the sample. The second part of the light, constituting reference light, passes through a reflector arm and is incident on the reference reflector. Both fractions of the light are reflected (the measuring light in the sample and the reference light at the reference reflector) and are guided back to the optical coupler along the same optical path (sample arm and reference arm respectively) where they are joined together and introduced through the detector arm to the detector. The light-sensitive surface of the detector can measure an interference signal caused by the interference between the two parts of the beam.

In order for an interference to occur, the optical path length in the reference arm (between the optical coupler and the reference reflector) differs by at most the coherence length of the light source from the optical path length of the measuring light between the optical coupler and the point of reflection in the sample. An interference signal is measured only if this condition is fulfilled. This fact is utilized to limit the investigation to one particular measuring depth, designated below as the LCI measuring depth, through appropriate adjustment of the length relationships between the reference arm and the sample arm.

This fundamental principle of the LCI measuring technique is used to allow various applications through variation of certain measurement details and through analysis of the interference signal.

For example, reference 1) concerns the investigation of the structure of optical fibers, in particular for localizing optical defects. References 2) and 3) concern various aspects of investigations in biological tissue (in particular skin tissue). These authors are only concerned with obtaining information in dependence on the LCI measuring depth defined by the interference criterion. These publications therefore perform a pure depth scan (also termed "longitudinal scan"), i.e. the length of the reference arm is varied to adjust the LCI measuring depth.

In contrast thereto, references 4) through 6) describe methods and apparatuses with which an additional lateral scan is carried out in order to obtain in various ways a picture of the distribution of the information of interest in the lateral direction (parallel to the surface of the sample) These methods therefore pertain to multi-dimensional imaging . In addition to a depth scan, a scan in at least one transverse direction ("lateral scan") is carried out. The invention is particularly concerned with methods and apparatuses for multi-dimensional imaging using the LCI principle (Optical Coherence Tomography (OTC)).

References 4) through 6) relate to OTC methods. Reference 4) pertains to a surface scan of a manufactured product and reference 5) concerns investigation of the eye, in particular the retina. Reference 6) provides particularly detailed discussion of multi-dimensional imaging of a sample using the LCI technique, in particular—as in the present invention—for applications involving the investigation of biological samples. The most important practical example discussed in reference 6) is investigation of the eye (as in reference 5)). The present invention primarily concerns investigations of samples having very finely distributed structures, in particular human skin.

The OTC method has particular advantages over other imaging methods (for example, ultrasound imaging, X-ray CT and lateral scanning confocal microscopes), since it does not utilize ionizing radiation and is therefore not damaging and since it facilitates high image resolution. It is particularly well suited for the investigation of relatively fine structures near to the surface. For the case of skin, the current state of development permits a maximum LCI measuring depth of approximately 1.5 mm. A spatial resolution better than 10 $\mu$m is possible in both the axial and lateral directions.

The methods known in the art through references 1) through 6) are difficult to perform and require a large amount of space in the range of the probe head. For these reasons, LCI apparatus have been proposed with which portions of the interferometer configuration (at least the optical coupler and the reference arm) are integrated into an optical chip (references 7) and 8).

An optical chip is an optical element made from a transparent material (normally glass) having integrated light guides. The light guides are made from a material having an index of refraction which is greater than that of the remaining optical chip. As is the case with optical fibers, the optical waveguide properties of the light guides integrated into the optical chip result from total internal reflection at the refractive index interface. Optical chips (also designated as integrated optical components) are primarily used for optical data transfer in optical fiber communication systems. Further details are given in comprehensive references such as "Optical Waveguides Advance to Meet Fiberoptic Demands", by E. D. Jungbluth, Laser Focus World, April 1994, 99–104 or the book "Integrated Optics", Proceedings of the Third European Conference, ECIO'85, H.-P. Noltes, R. Ulrich (Editors); Springer Verlag 1985 in which an article by P. O. Andersson et. al., "Fiber Optic Mach-Zehnder Interferometer Based on Lithium Niobate Components" is published on pages 26 through 28.

The measuring arm of an interferometer configuration always includes a part which is outside of the chip, namely the optical path between the light exit opening of the chip and the point of reflection in the sample. For this reason, the reference arm, which is completely integrated in the chip, is substantially longer than that portion of the measuring arm travelling through the chip. Since both arms depart from the same optical coupler, the reference arm cannot travel in a straight line through the optical chip. At least one beam deflection is necessary in order to accommodate the additional length by means of a zigzag or meandering travel of the reference arm in the optical chip.

Reference 7) describes two fundamental possibilities for effecting such a deflection. Firstly, a meandering curved optical waveguide can be used for the reference arm. Secondly, in addition to the reference reflector disposed at the end of the reference arm, at least one further reflector ("deflection reflector") can be provided to reflect the reference light from a first light guide into a second light guide. The light guides thereby constitute a first and a second partial path of the reference arm. The deflection reflector is conventionally formed by a slit in the waveguide produced by reactive ion etching. Since this manufacturing step is quite difficult, publication 7) considers the use of a deflection reflector to be disadvantageous and prefers circular-shaped deflection without reflectors.

In view of the above, the present invention is characterized in that the deflection reflector is provided on an end surface of the optical chip in such a manner that the reference light is cross-coupled between the two light guides which constitute portions of the reference arm.

The invention facilitates an extremely compact and simple assembly of a plurality of closely spaced interferometer configurations. In this fashion, multi-channel investigation of the sample is possible with the measuring light being irradiated into the sample at a plurality of closely spaced entrance locations of the interface. In consequence thereof, the integration time necessary for imaging with a particular desired resolution is reduced or an improved optical spatial (transverse and/or longitudinal) resolution is achieved for a given integration time.

It is easy to manufacture a reflector on the end surface of an optical chip. In principle, an arbitrary material having an index of refraction differing from that of the light guide can be applied onto the interface to cause reflection via a discontinuous change in the index of refraction. Metallic mirroring is however preferred for intensity reasons.

In order for the interferometer configuration to function, the light must cross-couple between the two light guides. That is to say, the light from one of the light guides which is incident on the reflecting surface should enter nearly completely (at least approximately 90%) into the other light guide and not be reflected back into the same light guide. Within the framework of the invention, several configurations are proposed in order to guarantee this cross-coupling.

For example, the cross-coupling can be achieved if both light guides are incident on the deflection reflector at an (identical) acute angle. A minimum angle (e.g. approximately 5°) relative to the normal to the surface is necessary in order to prevent disturbing reflection of portions of the light back into the same waveguide. In order to minimize intensity losses, it is necessary that in such an arrangement the deflection reflector is localized with very high precision at the crossing point of the two light guides. Procedures for accomplishing this will be described further below.

In accordance with a second configuration, complete cross-coupling of the reference beam from the first light guide into the second light guide is effected in that both waveguides travel parallel to another in a light coupling arrangement along a coupling length L immediately before the deflection reflector. The coupling length L is selected to effect cross-coupling. Towards this end, a phenomenon is used which is known in the art of light couplers and described in the publication 9) K. J. Ebeling: "Integrierte Optoelektronik"; Springer Verlag 1992, second edition, pages 146–151.

Two light guides are in a "light coupling arrangement" if they travel parallel to one another at a separation sufficiently small to effect coupling via mutual penetration of evanescent waves. A complete cross-coupling or switching over of the incident signal optical intensity is observed at a particular coupling length $L_c$ ("crossing condition"). At other lengths, varying portions of the light remain within the same light guide ("noncrossing condition") This is described in more detail below.

In general, the invention facilitates relatively simple production of compact interferometer configurations in optical chips. The technical problems associated with arrangement of the deflection reflector on an end surface of the optical chip can be solved in a manner allowing economical manufacture.

The separation between the probe head and the sample interface is varied for depth scanning. Towards this end, it is advantageous to focus the light penetrating into the sample with the assistance of an optical system disposed between the probe head and the sample interface in such a manner that the separation between the focal point inside the sample and the interface (designated below as "focus depth") coincides with the LCI measuring depth.

One thereby has the problem that the focus depth and the LCI measuring depth change differently when the separation between the probe head and the interface is changed. If the sample has an index of refraction N and the probe head is displaced by an amount z towards the sample, the LCI measuring depth is displaced to by a somewhat lesser amount, namely by $z_i'=z/N$. In contrast thereto, the same displacement of the probe head by an amount z causes an increase in the focus depth by approximately the factor N: $z_f'=z*N$ due to refraction at the interface. Despite this effect, a second principal feature of the invention, which is preferentially utilized in combination with the first principal feature but also has independent significance, provides for focus correction means to achieve agreement between the focus depth and the LCI measuring depth within the entire longitudinal scan range. These focus correction means guarantee that the focus depth changes equally along with changes in the LCI measuring depth. In this manner particularly good optical imaging quality is achieved within the entire depth scan range.

The invention is more closely described below with reference to the embodiments schematically represented in the figures.

Figure 2:
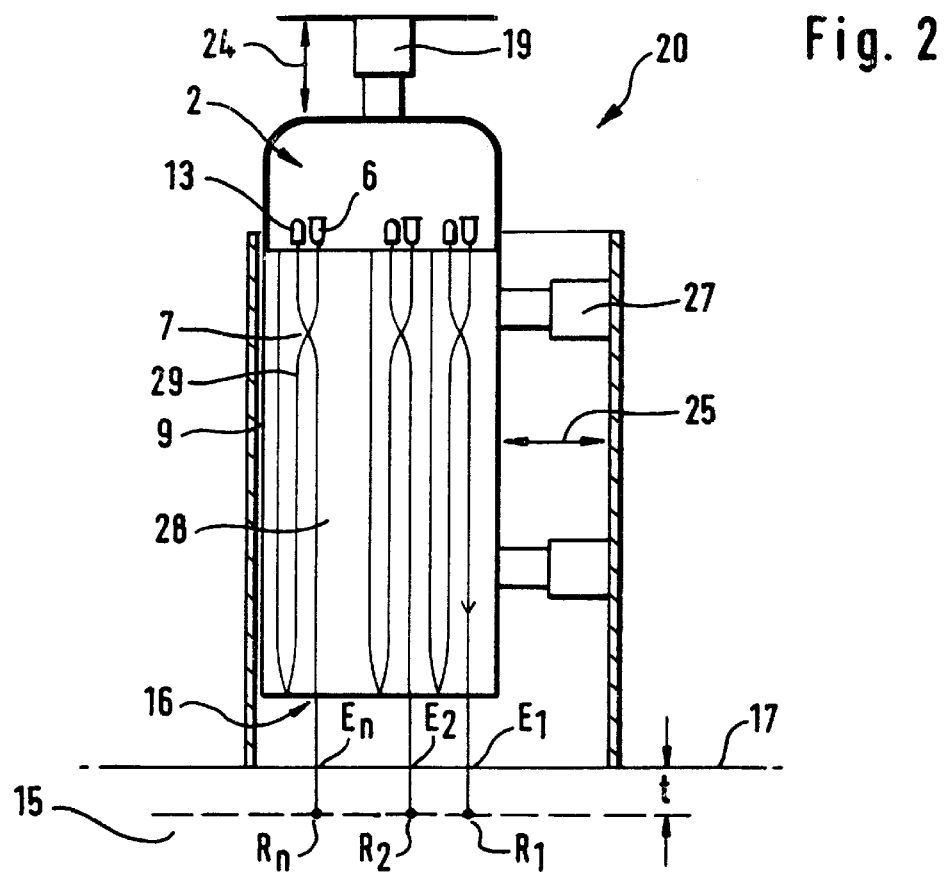
Figure 3A:
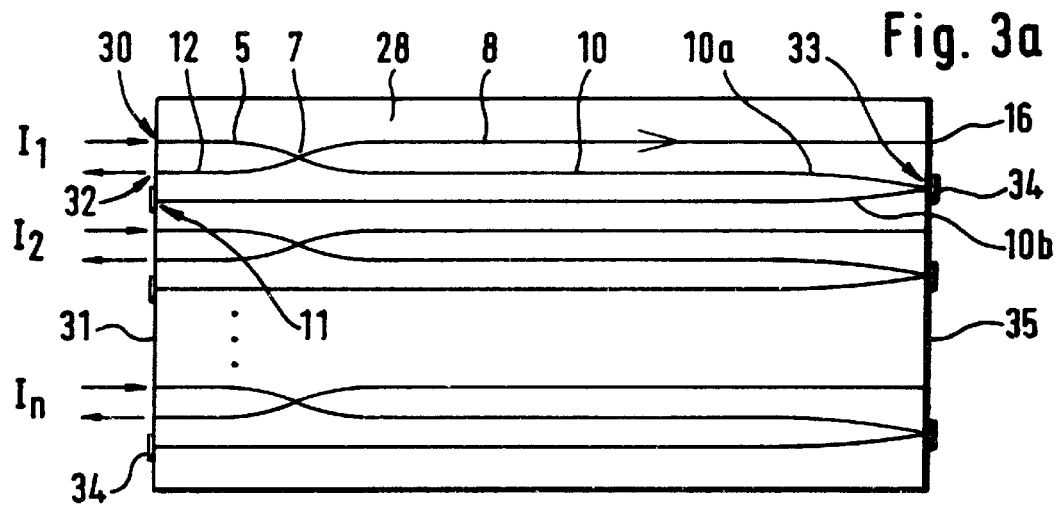
Figure 3B:
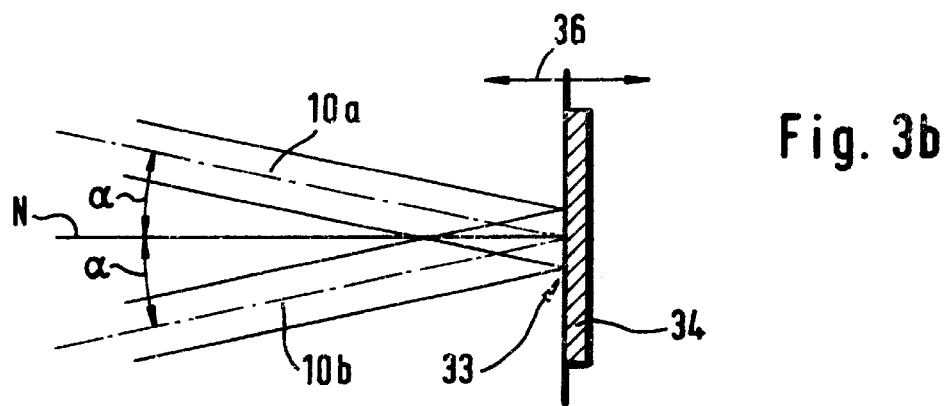
Figure 4:
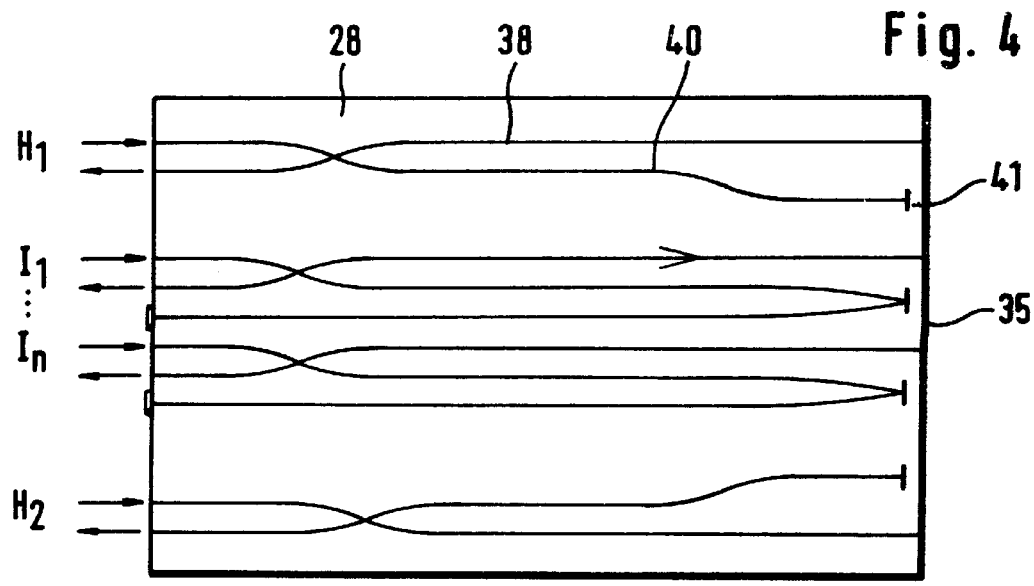
Figure 5A:
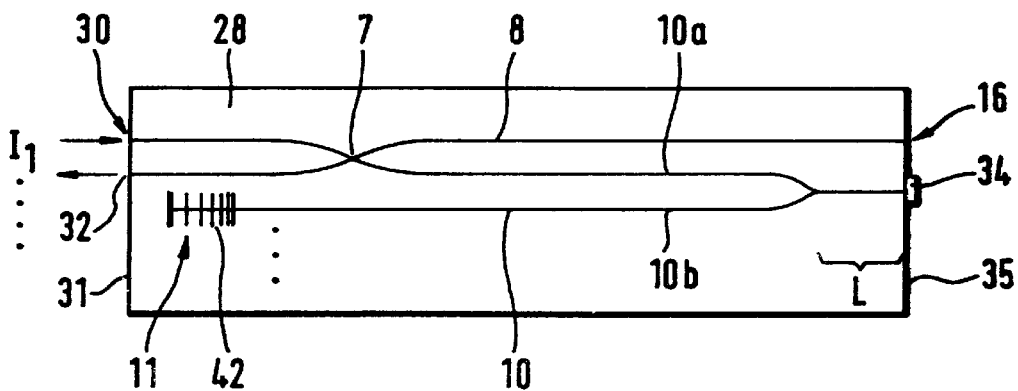
Figure 5B:
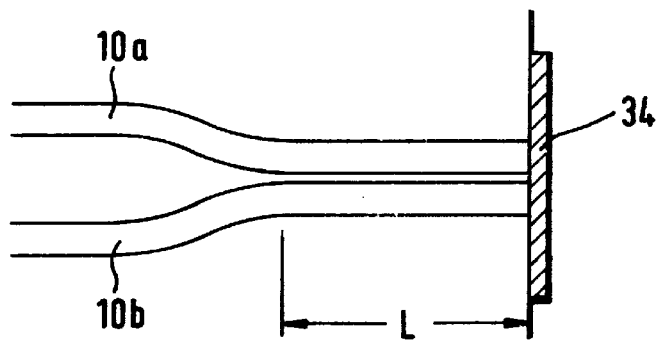
Figure 6:
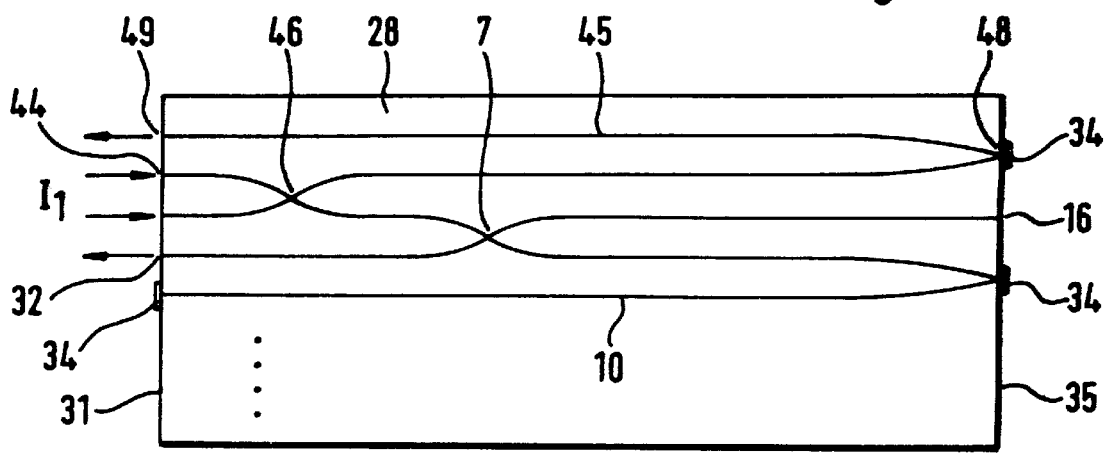
Figure 7:
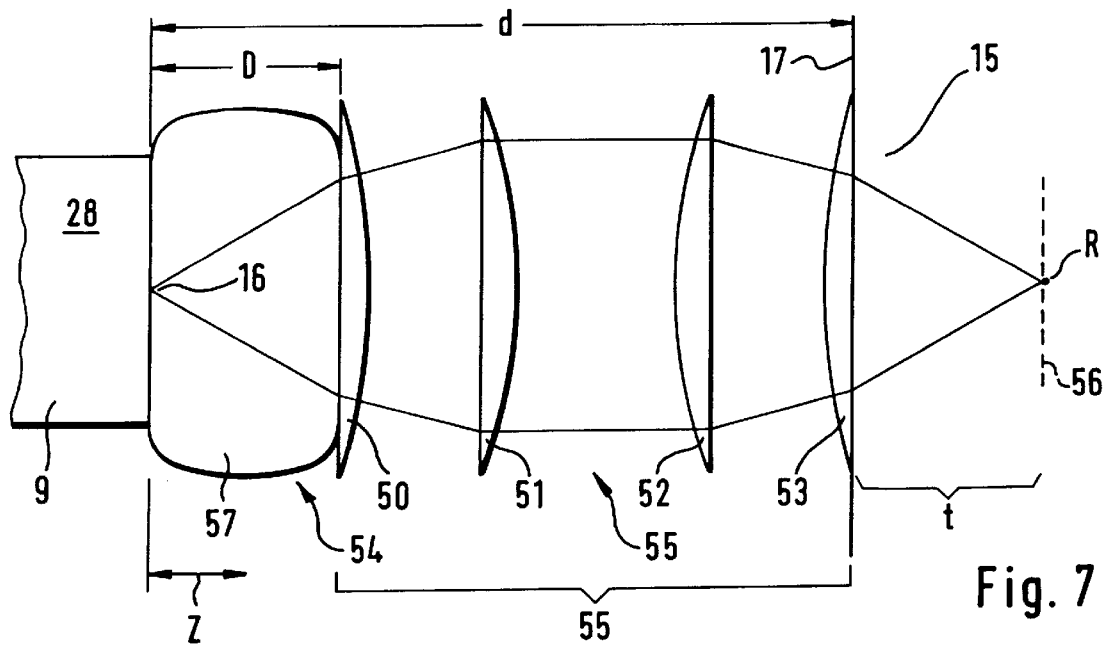
Figure 8:
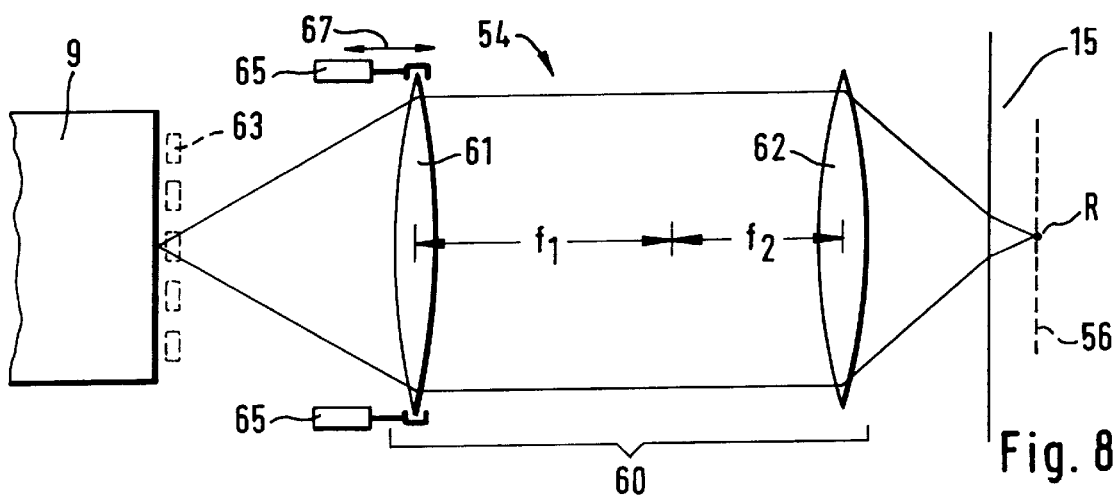
Figure 9:
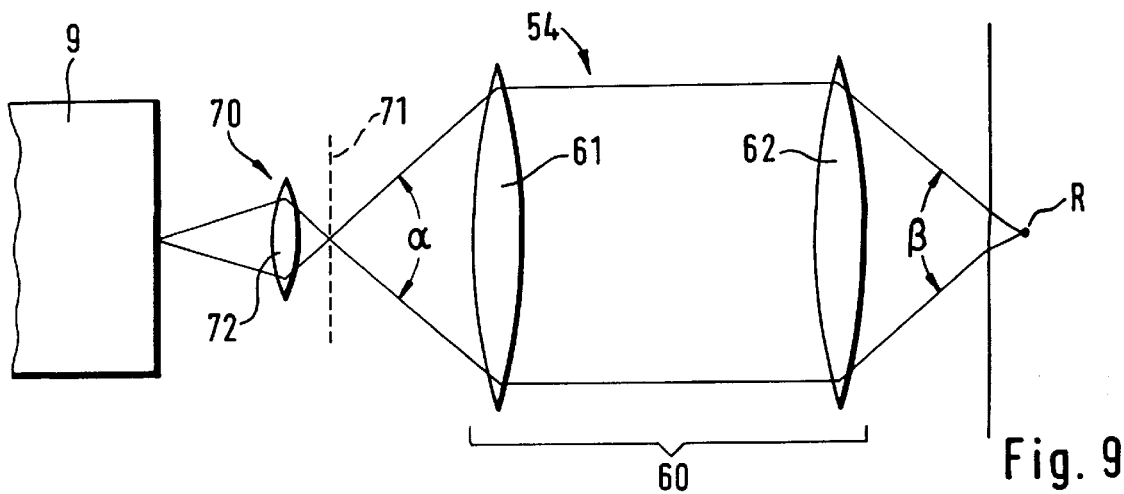
Figure 10:
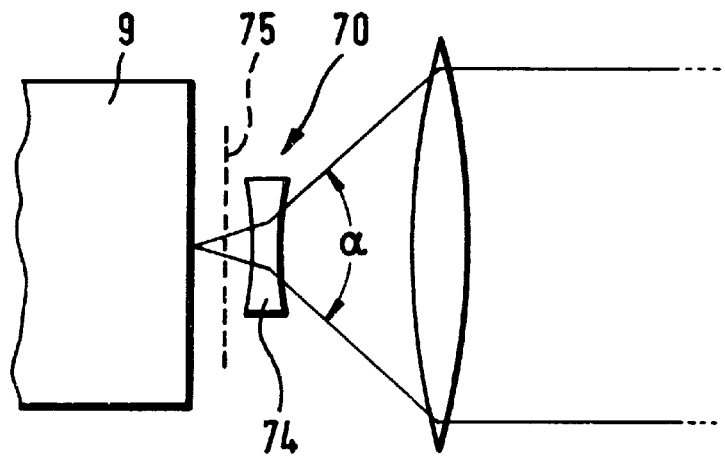
Figure 11:
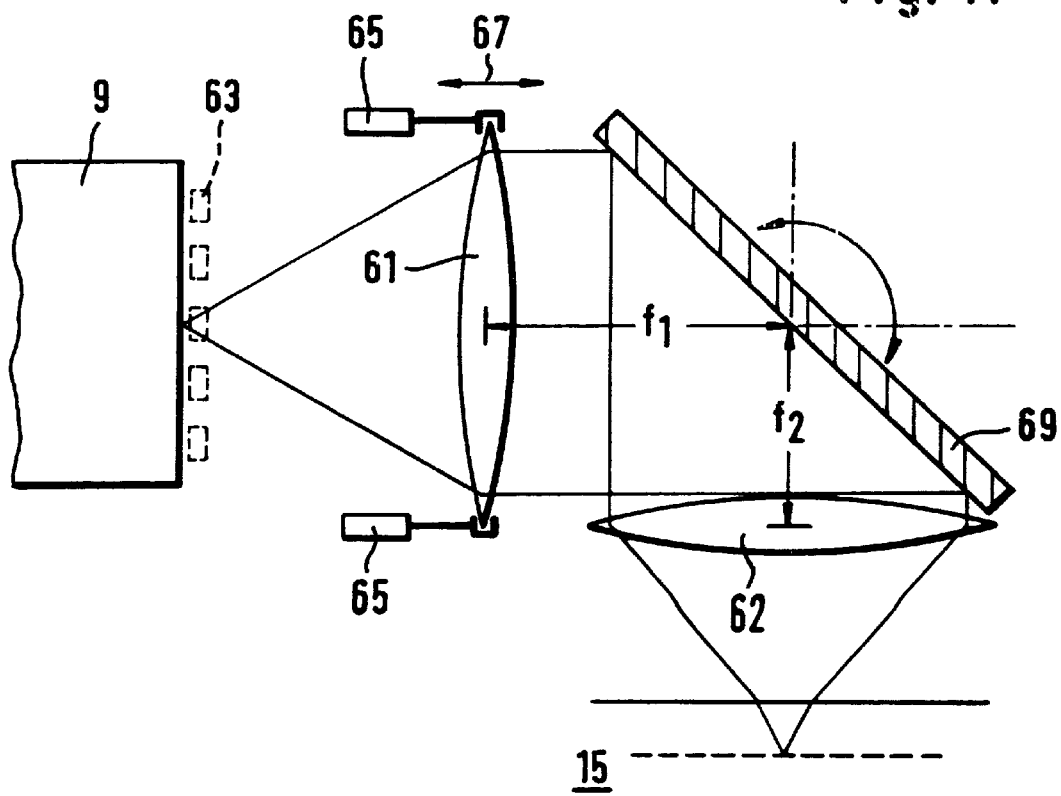

FIG. 1 shows a schematic representation of an LCI reflectometer according to prior art, FIG. 2 shows a cut through the scan module of an LCI reflectometer in accordance with the invention, FIG. 3a shows the waveguide pattern of a first embodiment of the optical chip, FIG. 3b shows an enlarged view of a portion of FIG. 3a, FIG. 4 shows the waveguide pattern of a second embodiment of the optical chip, FIG. 5a shows the waveguide pattern of a third embodiment of the optical chip, FIG. 5b shows an enlarged section of FIG. 5a, FIG. 6 shows the waveguide pattern of a fourth embodiment of the optical chip, FIG. 7 shows a first embodiment of an optical system having focus correction means in accordance with the invention, FIG. 8 shows a second embodiment of an optical system having a focus correction means in accordance with the invention, FIG. 9 shows an embodiment similar to FIG. 6 however with enlarged optical aperture, FIG. 10 shows a section of an embodiment alternative to FIG. 9, FIG. 11 shows an additional embodiment based on FIG. 8.

The LCI reflectometer 1 in accordance with prior art shown in FIG. 1 consists essentially of an interferometer configuration 2 and an electronic measuring and analysis unit 3. The interferometer configuration 2 comprises four interferometer arms: a light source arm 5 between a light source 6 and an optical coupler 7, a sample arm 8 between the optical coupler 7 and a probe head 9, a reference arm 10 between the optical coupler 7 and a reference reflector 11, and a detector arm 12 between the optical coupler 7 and the detector 13.

As mentioned, in order for an interference to occur, the optical path length of the measuring light between the optical coupler 7 and a reflection point R located within the sample 15 at an LCI measuring depth t below the interface 17 must correspond to the optical path length of the reference light between the optical coupler 7 and the reflecting surface of the reference reflector 11 (to within the coherence length of the light). If this interference condition is fulfilled, the detector measures an interference signal containing information about the sample at the measuring depth t. Phase modulation is often used in order to separate the interference signal from disturbing effects. For example, a light guide wound about a PZT (Piezo transducer) 22 can be provided in the sample arm for modulating the optical path length with a modulation frequency. Analysis of the measured signal of the detector 6 is done in a frequency selective manner using this modulation frequency.

In order to facilitate a depth scan in the sample 15, it is necessary for either the length of the reference arm 10 between the optical coupler 7 and the reference reflector 11 or the separation d between the light exit opening 16 of the probe head 9 and the interface (surface) 17 of the sample 15 to be variable. The first possibility (which has been used most often up to this point in time) is indicated in FIG. 1 with a dashed double arrow 18. In accordance with the invention, the separation d between the probe head 9 and the sample surface 17 is varied. Positioning means 19 serve for adjustment of the separation d for controlled and defined adjustment of the probe head 9 position relative to the sample 15. The unit comprising the probe head 9 and the positioning means 19 forms a scan module 20.

The light source 6, the detector 13, the PZT 22 and the positioning means 19 of the scan module 20 are connected to the electronic measuring and analysis unit 3. This unit contains conventional means for power supply to the light source 6, for processing the signal of detector 13 and for driving the positioning device 19.

Further description of the LCI method is given in the above mentioned references including description of extraction of various information concerning the sample from the interference signal. In the present invention conventional methods are used for processing and analysis of the measured signal. Reference therefor is made to citations 1) through 8).

FIG. 2 shows a scan module 20 for effecting the first principal aspect of the invention. A probe head 9 is disposed in the scan module 20 in such a manner that its location relative to the sample 15 is adjustable in both the longitudinal (perpendicular to interface 17, arrow 24) as well as the lateral (parallel to the interface 17, arrow 25) directions. The positioning means 19,27 necessary therefor are schematically indicated in the figure. These can e.g. comprise a conventional electromagnetic drive. An image slice through the sample along the lateral scan line can be realized using a one dimensional lateral scan. In the event that the positioning means 27 are adapted for two dimensional motion parallel to the interface 17, information can be obtained concerning that partial volume of the sample located beneath the scanned surface.

An optical chip 28 having waveguides 29 and constituting the main part of an interferometer configuration 2 is disposed within the probe head. Also belonging to this interferometer configuration are the light source 6 and detectors 13 which are disposed in such a manner that the light can be irradiated into and out of the waveguide paths 29 and such that the exiting light can be detected. Instead of the direct inward and outward irradiation shown here, transport from the respective light source and to the respective detector can often advantageously be effected via optical fibers ("fiber coupling").

Since the scanning should be as rapid as possible, the acceleration of various masses associated therewith can lead to disturbing vibrations. In order to avoid this, it can be advantageous to provide for a counterweight (not shown) within the scan module 20 whose mass corresponds to the moving mass of the optical chip 28 and which is moved in opposition to the optical chip.

FIG. 3a shows the waveguide pattern of an optical chip 28 having the main portions of the interferometer configuration, in particular the optical coupler 7 and the reference arm 10, both integrated into the chip. The part of the interferometer configuration integrated in the chip 28 is designated "interferometer module". In the preferred embodiment shown, a plurality of parallel interferometer modules $I_1 \ldots I_n$ are provided for in the same chip for multi-channel investigation of the sample. The measuring light enters at a plurality of entrance locations $E_1 \ldots E_n$ and is reflected at a plurality of reflection locations $R_1 \ldots R_n$ (FIG. 2). Each interferometer module I has a light input location 30 at which the light from a light source (not shown)—advantageously transported via an optical fiber—is coupled in. An output location 32 is disposed at the same front surface 31 of the optical chip 28 for coupling-out the light transported in the detector arm 12 to a detector (not shown).

The reference arm 10 must be longer than that part of the sample arm 8 integrated in the optical chip between the optical coupler 7 and the light exit opening 16. In addition to the reference reflector 11 disposed at the end of the reference arm 10, a deflection reflector 33 is therefore provided in the reference arm to deflect the reference light in the optical chip 28 in the opposite direction. In the embodiment shown in FIG. 3a, both reflectors 11,33 are mirrored end surfaces 34 on polished front surfaces 31,35 of the chip 28.

FIG. 3b shows an enlarged section in which, in this embodiment, the cross-coupling between the light guides 10a and 10b is effected by having same be incident on the deflection reflector 33 at an acute angle. The angle a with respect to the normal to the surface N is the same for both waveguides and should assume a value of at least 5° to guarantee sufficient complete cross-coupling. The longitudinal position of the deflection reflector 33 in the direction of the double arrow 36 must be located precisely at the crossing point of the light guides. The precision required for this positioning depends on individual requirements for the completeness of the cross-coupling and the extent to which slight losses in intensity can be tolerated. A required precision of +/-10 μm can be given as a guideline.

The number of interferometer configurations $I_1 \ldots I_n$ and the lateral separation of the light exit openings 16 can be chosen in accordance with the actual requirements. A particular advantage of the invention is that a very close separation is possible between light exit openings 16 and consequently between reflection points $R_1 \ldots R_n$ in the sample 15. Within the framework of LCI imaging, it is thereby possible to study a given investigation surface (FOV, "Field of View") with little or even no lateral mechanical motion. For example, a FOV of 1×1 mm² with 16 interferometer modules leads to a separation between light exit openings 16 of 62.5 μm at the front surface 25 of the optical chip 28 facing the sample. In consequence thereof, an optical resolution corresponding to this separation can be achieved without mechanical motion. Since conventional optical fibers have diameters of approximately 250 μm, the separation between the input locations 30 and the output locations 32 on the irradiation input front surface 31 of the optical chip must be larger so that a compression of the waveguide paths within the optical chip 28 is necessary. Equal lengths of the mutually corresponding waveguide paths in the interferometer modules $I_1 \ldots I_n$ can be easily effected through appropriate bending of the paths.

Even higher resolution can be achieved by laterally displacing the optical chip (as shown in FIG. 2). It is thereby also very advantageous if only a small lateral displacement (in the example given approximately 60 μm) is required. This can be accomplished with a high degree of reliability and speed using special piezo elements ("stacked piezo elements").

In general, the invention thereby facilitates a very dense configuration of the exit openings 16 of a plurality of interferometer configurations in one probe head 9. Applications of interest have opening separations of preferentially less than 0.5 mm.

As has already been stated, when producing an optical chip in accordance with FIGS. 3a and 3b, the reference reflector 33 must be precisely positioned at the crossing point of the light guides 10a and 10b. This requires an extremely precise cutting to length of the front surfaces 31 and 35 of the optical chip 28.

FIG. 4 shows one possibility for allowing this cutting. The optical chip 28 includes two auxiliary interferometer modules $H_1, H_2$ in addition to the interferometer modules $I_1 \ldots I_n$ (configured in the same manner as in FIG. 3). These are used for extension in the following manner.

In order to fulfill the interference condition in the auxiliary interferometers, the lengths of their sample arms 38 must correspond to the lengths of their reference arms 40. Due to the curved path, the reference arm 40 has a somewhat larger length than the sample arm 38. An element having a discontinuous change in refractive index is located at its end to form a (weak) reflector 41 at a position which exactly corresponds to the desired nominal position of the front surface 35. An interference signal is thereby produced by even a very small increase in the refractive index. When the front surface 35 is then ground down during the course of manufacture, an interference signal peak results when the length of the sample arm 38 coincides with the length of the reference signal 40. In this manner the nominal position of the front surface 35 can be precisely maintained. The second auxiliary interferometer $H_2$ facilitates a precise correction of the angular position of the front surface 35.

FIG. 5a shows a section of the waveguide pattern of an alternative embodiment of an optical chip 28, wherein only one single interferometer Ii is shown in this case. However, as in FIG. 3a, additional interferometer modules are preferentially integrated within the same optical chip 28.

In this embodiment, a sufficient cross-coupling between the light guides 10a and 10b is achieved by—as can be more clearly seen in FIG. 5b—having them travel parallel to another along a coupling length L in a light coupling device. The separation is sufficiently close (typically circa 15 μm) that mutual coupling occurs via evanescent waves. The coupling length L is selected to effect cross-coupling. As described in the above mentioned reference 9), complete cross-coupling is achieved at particular coupling lengths $L_c$. At intermediate lengths, varying fractions of light remain in the same light guide. The following formula has been given for the coupling lengths $L_c$ (in lower portion of page 149):

$$L_c = \frac{1}{Kappa}(2Ny - 1)\pi/2$$

with Kappa the coupling factor, and Ny an integer. The shortest length for complete cross-coupling is $$L_c = \frac{\pi}{2Kappa}$$

The configuration in accordance with the invention is different from that of the reference in that the deflection reflector which is oriented perpendicular to the two light guides reflects the light back into them. Complete cross-coupling requires the coupling length L along which the light guides travel parallel to another to be one half of Lc: L=Lc/2.

In practice, the coupling length L is empirically adjusted to maximize cross-coupling. This geometry has the substantial advantage that the degree of cross-coupling changes relatively little in dependence on the position of the reverse reflector so that the degree of precision required for positioning the reverse reflector is rather low.

An additional distinguishing feature of the embodiment shown in FIG. 5a is the use of a chirped grating 42 as the reference reflector 11. A chirped grating is a grating structure having a continuously increasing or decreasing grating constant. In this manner, light of shorter wavelength is reflected at the sections having smaller grating constants and longer wavelength light is reflected from sections having larger grating constants. Therefore, reflection from a chirped grating leads to differing fractions of light (necessarily polychromatic due to the low coherence) being reflected at differing locations of the grating. In the embodiment shown, e.g. the short wavelength portion of the light is reflected first at grid 42 (the grating constant increases in the direction of the incident light).

One can therefore take advantage of the properties of a chirped grating to compensate for optical dispersion. Optical dispersion is a problem in a high resolution LCI configuration, since the measuring light and the reference light are in part transported through differing media having differing dependencies for the light velocity and therefore for the index of refraction on the wavelength (dispersion). Therefore, the optical paths (product between the geometric path and the index of refraction) have differing lengths for differing wavelengths. This leads to a smearing-out of the interference signal and thereby to worse resolution in the longitudinal direction. Appropriate selection of the chirp ramp of the grating 42 of a chip grating can, to a good approximation, cause that all light portions travel the same optical path length as the measuring light independent of their wavelength, thereby to optimize the resolution.

Whether or not a chirped grating is used, it can be advantageous to dispose the reference reflector (e.g. in the form of ion etched structure) at another location on the optical chip rather than at the end surface of the optical chip (as in FIG. 3*a*).

The optical chip shown in FIG. 6 contains a modified interferometer configuration having an additional compensating optical path 45 for suppressing relatively large DC voltage portions of the detector signal. The compensating optical path 45 leads from an additional optical coupler 46 via a reflector 48 to an additional output location 49 on the front surface 31. In the embodiment shown, an additional input location 44 is also provided for input of light from another light source having e.g. a differing wavelength.

The light exiting at output locations 49 and 32 is detected by two detectors (not shown) connected to a compensation circuit. This conventional compensation technique is described e.g. in WO 92/19930. FIG. 6 shows the manner in which one can, in accordance with the invention, integrate the compensating optical path into the same optical chip in which the reference optical path travels.

FIGS. 7 through 9 show differing embodiments of focussing optical systems suitable for LCI reflectometers in which the depth scanning is effected through variation of the separation d between the probe head 9 and the interface 17. Focus correction means 54 are provided in each case to guarantee that the focus depth in the sample 15 always changes equally with changes in the LCI measuring depth t. In this manner, a sharp focus is achieved at each point of the depth scan.

FIG. 7 shows a probe head 9 preferentially comprising an optical chip 28 in accordance with one of those in FIGS. 2 through 6. An optical system 55 comprising a plurality of lenses 50 through 53 causes each light exit point 16 of the probe head 9 to be imaged in a focal plane 56. In order to guarantee optimal optical resolution, the reflection point R to which the LCI scan is adjusted should lie in the focal plane 56 of the optical system 55 for the entire scan range. This is not the case in the absence of additional focus correction means, since (for an index of refraction N>1, which is always the case in practice) a displacement of the probe head 9 by an amount z leads to a different displacement of the focal plane 56 and the reflection point R (in other words, to different changes in the focus depth and the LCI measuring depth). The LCI measuring depth changes less than z and the focus depth by more than z.

In the embodiment shown in FIG. 7, the focus correction is effected via a fluid-filled, transparent bubble 57 disposed in the optical path of the measuring light between the probe head 9 and the sample 15 in such a manner that its thickness decreases when the probe head is moved towards the sample. The fluid in the bubble 57 should thereby have an index of refraction as similar as possible to the index of refraction of the sample 15. Movement of the probe head 9 by an amount z causes the thickness D of the bubble 57 to decrease by the same amount to displace both the focal plane 56 as well as the LCI reflection point R in the sample towards the right.

FIG. 8 shows a particularly preferred embodiment with which the focus correction is achieved using purely optical means. Here, the optical focus correction system 60 comprises two lenses 61,62 whose separation is as large as the sum of their focal lengths f1 and f2. A configuration of this kind is used in Keppler telescopes and is designated as a Keppler system. The lenses 61 and 62 can be simple lenses or multi-lens systems.

The focus correction results when the focal lengths $f_1$ and $f_2$ of lenses 61 and 62 are chosen in consideration of the index of refraction N in the sample according to the formula $f_2/f_1=1/N$. This geometric imaging condition leads to a correction in the depth direction by a factor $1/N^2$. In this manner, a displacement of the probe head 9 by z no longer leads to an extension in the sample by a factor N, rather to shortening by the factor $1/N^{2*}N=1/N$. The focus depth therefore changes equally with the LCI measuring depth which is likewise shortened by 1/N.

In an embodiment of this kind an additional improvement in focussing is possible if one of the lenses in the Keppler system is adjustable by a small amount (for example up to 20 $\mu$m) in the longitudinal direction (double arrow 67) with the assistance of a positioning drive 65 (e.g. a piezo drive). When focussing, it is thereby possible to take into consideration the fact that the index of refraction changes in differing layers of skin so that the average index of refraction is not constant for changes in the LCI measuring depth t. Adjustment of a lens effects appropriate compensation in each case.

In FIGS. 7 and 8, there is only one optical system 55 or 69 for all interferometer modules so that all light exit openings of the probe head 9 are imaged in the plane 56. Only one optical path is shown for reasons of clarity.

In order to compensate for correction errors in the relatively large lenses of optical systems 55 and 60, individual small lenses 63 (dashed representation in FIG. 8) can be advantageously disposed in front of each light exit opening 16 in such a manner as to compensate for imaging distortions of the large lenses.

In the embodiment of FIG. 8, the relationship between the focal lengths of the two lenses 61 and 62 determines the optics and thereby the magnification. Therefore the optical aperture on the sample side cannot be easily enlarged for a given relatively small aperture at the input side of the optical system. A large optical aperture on the sample side can however be desirable, in particular for improving the optical resolution of the depth scan.

In order to accomplish this, an additional optical imaging system 70 shown in FIG. 9 can be advantageously provided upstream from the optical system 60 in accordance with FIG. 8, this additional optical system being movable together with the probe head 9. This system produces a scaled down image of the light exit opening 16 and of the probe head 9 in the object plane of the Keppler system (i.e. in the input side focal plane of lens 61). In this manner, the aperture angle $\alpha$ is increased at the input side of the focus correction system 60 and thereby the aperture angle $\beta$ on its sample side.

The same effect of the additional optical imaging system 70 can, as shown in FIG. 10, be achieved using a concave lens 74 rather than a convex lens 72. In this case, a scaled down virtual image is produced in a plane 75 at that side of the concave lens facing the probe head instead of the real image in the plane 71 shown in FIG. 9. The purpose of lenses 72,74 can also be achieved by micro-lenses which (such as lenses 63 in FIG. 8) are each associated with one interferometer configuration.

The optical systems 55 and 60 are disposed in a stationary manner in a particular position at the interface 17 of sample 15. Only the probe head 9 must be moved for scanning. In accordance with the invention, the focussing optical system should generally be substantially stationary to effect as small an amount of moving mass as possible. This does not of course preclude a micro-positioning of lenses as e.g. effected by positioning drive 65 in FIG. 8. Such a positioning (of up to at most 0.02 mm) can be rapidly and precisely effected using e.g. piezoelectric elements.

Within this context, especially the actual focus correction system should be "stationary", i.e. the Keppler system 60 for the case of FIGS. 8 through 10. Movement of the optional upstream correction lenses 63,72,74 together with the probe head 9 is much easier to realize, since these lenses are rather small and of low mass. The mass fraction of the optical elements of the entire imaging system which move together with the probe head 9 should however be as small as possible (less than 20%, preferentially less than 5%).

The embodiments in accordance with FIGS. 8 through 10 facilitate a particularly simple realization of the lateral scanning needed for an OCT system. FIG. 11 shows that a pivoting mirror 69 can be disposed between the lenses 61 and 62 in such a manner that the required lateral displacement of the image can be effected with a very small pivot motion to optically scan.

What is claimed is:

1. Low coherence interferometer apparatus for investigation of a sample, in particular for purposes of multi-dimensional imaging, having an interferometer configuration comprising a low coherence light source, a probe head having a light exit opening for irradiating light into the sample, an optical coupler, a reference reflector and a detector wherein the optical paths between the elements of the interferometer configuration form interferometer arms, namely a light source arm between the light source and the optical coupler, a sample arm between the optical coupler and the sample, a reference arm between the optical coupler and the reference reflector, and a detector arm between the optical coupler and the detector, measuring light is irradiated into the sample via the light source arm and the sample arm and through an interface defining the sample and light reflected from inside the sample is guided to the detector via the sample arm and the detector arm, reference light is-guided from the optical coupler to the reference reflector and therefrom via the reference arm and the detector arm to the detector, the measuring light and the reference light are joined in such a manner that they are both incident on the detector at the same location to produce an interference signal, wherein light reflected at an LCI measuring depth beneath the interface of the sample is selectively detected, and the optical coupler and the reference arm of the interferometer configuration are commonly integrated in an optical chip, wherein the reference arm has, in addition to the reference reflector, a deflection reflector by means of which the reference light from a first light guide forming a first partial path of the reference arm is reflected into a second light guide forming a second partial path of the reference arm to achieve a sufficient reference light path length in the optical chip, and wherein the deflection reflector is formed at an end surface of the optical chip in such a fashion that the reference light is cross-coupled between the two light guides, positioning means are provided for depth scanning the sample by changing the separation between the probe head and the interface, an optical system is disposed between the probe head and the interface for focusing light irradiated into the sample in a focal plane at a focal depth whose separation from the interface coincides with the LCI measuring depth, and the optical system comprises focus correction means for matched changing of the focal depth during the depth scan in such a manner that the focal depth and the LCI measuring depth coincide within the depth scanning range of the system.

2. Apparatus according to claim 1, wherein the deflection reflector is formed by a mirrored end surface of the optical chip.

3. Apparatus according to claim 1, wherein the first light guide and the second light guide are incident on the deflection reflector at an acute angle $\alpha$ to cross-couple the reference light.

4. Apparatus according to claim 1, wherein the first light guide and the second light guide travel parallel to one another in a light coupling device along a coupling length L directly before the deflection reflector, wherein the coupling length L is adapted to effect cross-coupling.

5. Apparatus according to claim 1, wherein the optical chip comprises a plurality of parallel disposed interferometer modules for multi-channel investigation of the sample, wherein the measuring light is irradiated into the sample at a plurality of interface input locations.

6. Apparatus according to claim 1, wherein the optical chip in the reference arm comprises a chirped grating.

7. Apparatus according to claim 1, wherein the optical chip comprises an interferometer module having an additional compensating optical path a portion of the light from the light source being branched-off by means of an additional optical coupler and guided to an additional light detector for compensation of portions of light which are incapable of interference.

8. Apparatus according to claim 1, wherein positioning means are provided for lateral scanning to change the position at which the measuring light is irradiated through the interface into the sample in at least one spatial direction parallel to the interface.

9. Apparatus according to claim 1, wherein positioning means are provided to change the separation of the probe head from the interface for depth scanning.

10. Low coherence interferometer apparatus for investigation of a sample, in particular for purposes of multi-dimensional imaging, having an interferometer configuration comprising a low coherence light source, a probe head having a light exit opening for irradiating light into the sample, an optical coupler, a reference reflector and a detector wherein the optical paths between the elements of the interferometer configuration form interferometer arms, namely a light source arm between the light source and the optical coupler, a sample arm between the optical coupler and the sample, a reference arm between the optical coupler and the reference reflector, and a detector arm between the optical coupler and the detector, the measuring light is irradiated into the sample via the light source arm and the sample arm through an interface defining the sample and light reflected from inside the sample is guided to the detector via the sample arm and the detector arm, reference light is guided from the optical coupler to the reference reflector and therefrom via the reference arm and the detector arm to the detector, the measuring light and reference light are joined in such a manner that they are both incident on the detector at the same location to produce an interference signal, wherein light reflected from an LCI measuring depth beneath the interface of the sample is selectively detected, wherein positioning means are provided for depth scanning the sample by changing the separation between the probe head and the interface, an optical system is disposed between the probe head and the interface for focussing light irradiated into the sample in a focal plane at a focal depth whose separation from the interface coincides with the LCI measuring depth, and the optical system comprises focus correction means for matched changing of the focal depth during the depth scan in such a manner that the focal depth and the LCI measuring depth coincide within the depth scanning range of the system.

11. Apparatus according to claim 10, wherein the focus correction means comprise a movable transparent bubble filled with liquid disposed in the optical path of the measuring light between the probe head and the sample in such a manner that its thickness decreases when the probe head is moved towards the sample.

12. Apparatus according to claim 10, wherein the focus correction means comprise a Keppler system having two lenses whose separation corresponds to the sum of their focal lengths with the following relationship obtaining for the focal lengths $f_1$ and $f_2$:

$$f_2/f_1 = 1/N,$$

with N corresponding approximately to the average index of refraction of the sample (15).

13. Apparatus according to claim 10, wherein the optical system comprises a stationary lens system.

* * * * *